United States Patent [19]
Huang

[11] Patent Number: 5,648,378
[45] Date of Patent: Jul. 15, 1997

[54] 2-IMINOCHROMENE DERIVATIVES AS INHIBITORS OF PROTEIN TYROSINE KINASE

[75] Inventor: Chi-Kuang Huang, Farmington, Conn.

[73] Assignee: Research Corporation Technologies, Inc., Tucson, Ariz.

[21] Appl. No.: 472,192

[22] Filed: Jun. 7, 1995

[51] Int. Cl.[6] ............................ C07D 311/76; A61K 31/35
[52] U.S. Cl. ................................................ 514/456; 549/404
[58] Field of Search ........................... 549/404; 514/456

[56] References Cited

FOREIGN PATENT DOCUMENTS

| | | |
|---|---|---|
| WO93/16064 | 8/1993 | WIPO. |
| WO93/16084 | 8/1993 | WIPO. |
| WO94/03432 | 2/1994 | WIPO. |

OTHER PUBLICATIONS

J. M. Bishop, "Cellular Oncogenes and Retroviruses," *Ann. Rev. Biochem.*, 52, 301–354 ©(1983).

J. B. Bolen et al., "Activation of pp60$^{c-src}$ protein kinase activity in human colon carcinoma," *PNAS USA*, 84, 2251–2255 (Apr., 1987).

T. R. Burke, Jr., "Protein–tyrosine kinase inhibitors," *Drugs of the Future*, 17, 119–131 ©(1992).

T. R. Burke, Jr., et al., "Bicyclic Compounds as Ring–Constrined Inhibitors of Protein–Tyrosine Kinase p56$^{lck}$," *J. Med. Chem.*, 36, 425–432 (Feb. 1993).

V. Cleghorn et al., "Raf–1 Interacts with Fyn and Src in a Non–Phosphotyrosine–dependent Manner," *J. Biol. Chem.*, 269, 17749–17755 (Jul. 1994).

M. Cross et al., "Growth Factors in Development, Transformation, and Tumorigenesis," *Cell*, 64, 271–280 (Jan. (1991).

B. Ek et al., "Stimulation of Tyrosine–Specific Phosphorylation by Platelet–derived Growth Factor," *Nature*, 295, 419–420 (Feb. 1982).

P. Fanning et al., "Elevated Expression of pp60$^{c-src}$ in Low Grade Human Bladder Carcinomas," *Cancer Res.*, 52, 1457–1462 (Mar. 1992).

D. W. Fry, "Protein Tyrosine Kinases as Theraputic Targets on Cancer Chemotherapy and Recent Advances in the Development of New Inhibitors," *Exp. Opin. Invest. Drugs*, 3, 577–595 ©(1994).

T. Hunter et al., "Protein–Tyrosine Kinases," *Ann. Rev. Biochem.*, 54, 897–930 ©(1985).

S. Jacobs et al., "Somatomedin–C Stimulates the Phosphorylation of the b–Subunit of Its Own Receptor," *J. Biol. Chem.*, 258, 9581–9584 Aug. (1983).

M. Kasuga et al., "Insulin Stimulates the Tyrosine Phosphorylation of the Insulin Receptor in a Cell–Free System," *Nature*, 298, 997–669 Aug. (1982).

D. K. Luttrell et al., "Involvement of pp60$^{c-src}$ with Two Major Signalling Pathways in Huma Breast Cancer," *PNAS USA*, 91, 83–87 (Jan. 1994).

S. A. Lynch et al., "Increased Expression of the src Proto–Oncogene in Hairy Cell Leukemia and a Subgroup of B–Cell Lymphomas," *Leukemia*, 7, 1416–1422 (Sep. 1993).

M. E. Marshall et al., "Growth–inhibitory Effects of Coumarin (1,2–Benzopyrone) and 7–Hydroxycoumarin on Human Malignant Cell Lines In Vitro," *J. Cancer Res. Clin. Oncol.*, 120(Suppl.), S3–S10 ©(1994).

C. N. O'Callaghan et al., "Anticancer Agents XIII. Synthesis and Antitumour Activity of 2–Iminochromene Derivatives," *Proc. Royal Irish Acad.*, 79, 87–93 Mar. (1979).

C. N. O'Callaghan et al., "2–Alkyl–5–imino–1–Benzopyrano[3,4–c]pyridin–4(3H, 5H)–ones and Related Compounds from Reaction of 3–Carbamoyl–2–Iminochromens with Methyl Ketones," *J. Chem. Soc. Perkins Trans.*, I, 2273–2276 ©(1981).

A. E. Ottenhoff–Kalff et al., "Characterizationof Protein Tyrosine Kinases from Human Breast Cancer: Involvement of the c–src Oncogene Product," *Cancer Res.*, 52, 4773–4778 (Sep. 1992).

R. D. Thornes et al., "Treatment with Coumarin to Prevent or Delay Recurrence of Malignant Melanoma," *J. Cancer Res. Clin. Oncol.*, 120(Suppl.), S32–S34 ©(1994).

A. Ulrich et al., "Signal Transduction by Receptors with Tyrosine Kinse Activity," *Cell*, 61, 203–212 Apr. (1990).

H. Ushiro et al. "Identification of Phosphotyrosine as a Product of Epidermal Growth Factor–Activated Protein Kinase in A–431 Cell Membranes," *J. Biol. Chem.*, 255, 8363–8365 Sep. (1990).

P. Workman et al., "Tyrosine Kinase Inhibitors," *Sem. Cancer Biol.*, 3, 369–381 ©(1992).

Y. Yarden et al., "Growth Factor Receptor Tyrosine Kinases," *Ann. Rev. Biochem.*, 57, 443–478 ©(1988).

*Primary Examiner*—Johann Richter
*Assistant Examiner*—Laura L. Stockton
*Attorney, Agent, or Firm*—Schwegman, Lundberg, Woessner & Kluth, P.A.

[57] ABSTRACT

Protein tyrosine kinase inhibitors are provided of formula (I):

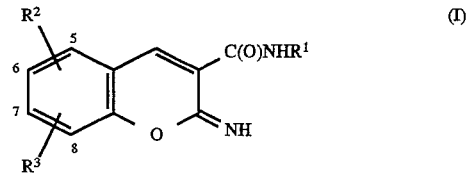

wherein $R^2$ is H, OH, halo or $O(C_1-C_4)$alkyl; $R^2$ is OH, halo or $O(C_1-C_4)$alkyl; $R^1$ is

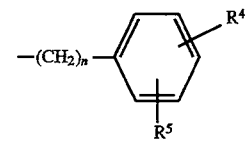

wherein $R^4$ is H, OH, halo, $CH_2OH$, $C(O)CH_3$, $C(O)N(R)_2$ wherein each R is H or $(C_1-C_4)$alkyl; or $C(O)R$ wherein $R^6$ is OH or $O(C_1-C_4)$alkyl; and $R^5$ is OH, $CH_2OH$, $C(O)CH_3$, $C(O)N(R)_2$ or $C(O)R^6$; or a pharmaceutically acceptable salt thereof, which inhibit the pathological proliferation or growth of mammalian cells, such as cancer cells.

24 Claims, No Drawings

2-IMINOCHROMENE DERIVATIVES AS INHIBITORS OF PROTEIN TYROSINE KINASE

The present invention was made with the support of the Government under NIH Grant No. AI20943. The U.S. Government has certain rights in the invention.

BACKGROUND OF THE INVENTION

Cell growth is controlled, to a large degree, by extracellular ligands which bind to specific receptors on the surface of cells. Cross et al., *Cell*, 64, 2172 (1991). A number of these receptors, including the epidermal growth factor (EGF) receptor, have intrinsic protein tyrosine kinase (PTK) activity. Yarden et al., *Ann. Rev. Biochem.*, 57, 443 (1988). Ligand-dependent activation of receptor associated tyrosine kinases or unregulated synthesis of tyrosine kinase oncoproteins results in tyrosine phosphorylation of cellular substrates which have a critical role in the control of mitogenesis, cell cycle regulation, cell survival and cellular transformation. Ullrich et al., *Cell*, 61, 203 (1990).

Among the cellular enzymes that are involved in signal transduction, the protein tyrosine kinases (PTKs) appear to play key roles in the initiation of various signaling cascades. PTKs can be divided into two major groups on the basis of their predicted structures. The first PTK group, which contains those that possess extracellular domains which generally function to bind peptide hormones, are the receptor PTKs. Examples of PTKs included in this group are the receptors for epidermal growth factor, the nerve growth factor and platelet-derived growth factor.

The second PTK group comprises those that lack the extracellular domains and are referred to as nonreceptor PTKs, even though many members of this group appear to be associated, albeit noncovalently, with some type of cell surface ligand-binding protein. Members of this group include the Src family of PTKs as well as the members of the fes/fps and abl gene families. The nonreceptor class of PTKs is growing with regard to the number of enzymes it includes, which are also demonstrating surprising diversity in predicted structure.

The Src family of nonreceptor PTK enzymes currently contains nine members: Src, Yes, Fyn, Lyn, Lck, Hck, Fgr, Blk, and Yrk. The Src, Yes, Fyn, and Lyn proteins are expressed in a variety of cell types, whereas the Lck, Hck, Fgr and Blk proteins are expressed primarily in different types of hematopoietic cells. Also, Src is expressed by the cells associated with colon cancer, breast cancer and ovarian cancer as well as virtually all other forms of human cancer. Likewise, Fyn and Lyn are expressed in virtually all forms of human cancer.

Tyrosine-specific protein kinase activity is also known to be associated with oncogene products of the retroviral Src gene family. Hunter et al., *Annu. Rev. Biochem.*, 54, 897 (1985). This kinase activity is strongly correlated with the ability of retroviruses to transform cells, since mutants with reduced kinase activity have lower transforming efficiency, and mutants which lack tyrosine kinase activity are transformation defective. Bishop, *Annu. Rev. Biochem.*, 52, 301 (1983). Similar kinase activity is also associated with the cellular receptors for several growth factors such as EGF, platelet derived growth factor, insulin, and insulin-like growth factor I. Ushiro et al., *J. Biol. Chem.*, 255, 8363 (1980); Ek et al., *Nature*, 295, 419 (1982); Kasuga et al., *Nature*, 298, 667 (1982); Jacobs et al., *J. Biol. Chem.*, 258, 9581 (1983). Therefore, it is likely that tyrosine phosphorylation plays an important role for cell proliferation and malignant cell transformation, and a drug capable of PTK inhibition would be likely to exhibit desirable antiproliferative, pro-differentiating effects. Therefore, PTKs represent potential targets for the development of anti-cancer drugs or drugs intended to control pathologies associated with abnormal cellular proliferation.

A number of PTK inhibitors have been investigated as potential anticancer reagents. They include isoflavones (genistein), tyrphostins (erbstatin), lavendustin analogues, staurosporine analogues (dianilinophthalmides), polyhydroxylated stilbene analogues of piceatannol, dithiobis (indole-alkanoic acid), dihydroxyisoquinolines and others. For example, see T.R. Burke, Jr., "Protein-tyrosine kinase inhibitors," *Drugs of the Future*, 17, 119 (1992); P. Workman et al., *Seminars in Cancer Biology*, 3, 369 (1992); and D.W. Fry, *Exp. Opin. Invest. Drug*, 3, 577 (1994).

For the purpose of obtaining highly specific inhibitors, bicyclic compounds as ring-constrained inhibitors of PTK have recently been introduced. They are expected to interact with the flat, cleft-like catalytic cavity of the kinase domain with high specificity. Iminochromenes belong to this type of compound. For example, several 3-carbamoyl-2-iminochromenes with weak PTK inhibitory activity toward $p56^{lck}$ have been reported by T.R. Burke et at., *J. Med. Chem.*, 36, 425 (1993). These compounds are of general formula (1):

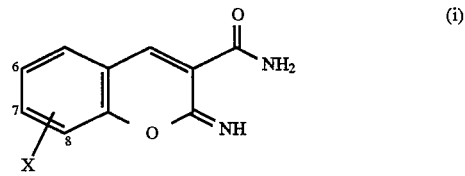

wherein X is 6-, 7- or 8-hydroxy or 6,7 or 7,8-dihydroxy. Earlier, C. N. O'Callaghan et al., *Proc. R.I.A.*, 79, 87 (1979) reported that compounds of formula (1) wherein X is 6- or 8-methoxy, 6-chloro, 6-nitro or 8-ethoxy exhibited anti-tumor activity against P388 murine lymphocytic leukemia. G. Keri et al. (published PCT application WO 93/16084) disclose compounds of formula (1) wherein X represents up to four benzo-substituents, including trihydroxy or trialkoxy. These compounds are generally disclosed to be anti-tumor agents due to their ability to inhibit TK enzymes. However, no biological data was reported for these compounds.

Therefore, a need exists for selective TK inhibitors which broadly inhibit the pathological division of cells, such as tumor cells, without exhibiting undesirable cytotoxicity to normal cells.

SUMMARY OF THE INVENTION

The present invention provides compounds of formula (I)

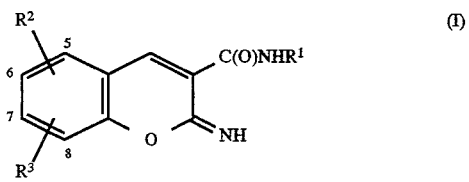

wherein $R^2$ is H, OH, halo or $O(C_1-C_4)$alkyl; $R^3$ is OH, halo or $O(C_{1-C4})$alkyl; and $R^1$ is

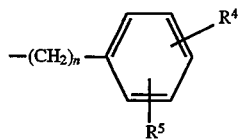

wherein n is 0–12, preferably 0–4; $R^4$ is H, OH, halo, $O(C_{1-C4})$alky)$CH_2OH$, $C(O)CH_3$, $C(O)N(R)_2$, wherein each R is H, $(C_1-C_4)$alkyl or phenyl or $C(O)R^6$, wherein $R^6$ is OH or $O(C_1-C_4)$alkyl; and $R^5$ is OH, halo, $O(C_1C_4)$alkyl $CH_2OH$, $C(O)CH_3$, $C(O)N(R)_2$, or $C(O)R^6$, and the pharmaceutically acceptable salts thereof. As drawn, —$R^2$, —$R^3$, —$R^4$, and —$R^5$ can occupy any available position on their respective rings. Preferably, when one of $R^2$ and $R^3$ is $O(C_1-C_4)$alkyl and the other is H; and $R^4$ is H and $R^5$ is OH or halo, $R^4$ is 3'-OH, 4'-OH, or 5'-OH or 3'-halo, 4'-halo, or 5'-halo. Halo is Cl, Br, F or I.

These compounds are inhibitors of the activity of the 60-kDa src gene product, p60$^{c-src}$ kinase. D. K. Luttrell et al., *PNAS USA*, 91, 83 (1994) have reported that p60$^{c-src}$ kinase may be involved with two major signaling pathways in human breast cancer cells. It binds to activated epidermal growth factor receptor and to p185HER2/neu. It also interacts with raf-1 in a non-phosphotyrosine-dependent manner. (V. Cleghern et al., *J. Biol. Chem.*, 269, 17749 (1994). Its activity is elevated in many tumors. See, for example, J.B Bolen et al., *PNAS USA*, 84, 2251 (1987) (colon carcinoma); S.A. Lynch et al., *Leukemia*, 7, 1416 (1993) (hairy cell leukemia, B-cell lymphoma); A.E. Ohenhoff-Kalff et al., *Cancer Res.*, 52, 4773 (1992) (breast cancer); and P. Fanning et al., *Cancer Res.*, 52, 1457 (1992) (bladder carcinoma).

Therefore, the present invention also provides a method to inhibit TK activity in populations of mammalian cells having cell surface receptors associated with TK activity. The preselected cell population is contacted either in in vivo or in vitro with a compound of the invention, in an amount effective to inhibit the TK activity, and thus, the cellular events associated with TK activity, in said population. It is expected that the compounds of the present invention will be effective in the treatment of diseases or pathologies associated with the pathological proliferation of mammalian cells such as B-cells, NK cells and T-cells, either used alone or in combination with immunotoxins or with conventional therapies for such afflictions. Such pathologies include other cancers, such as acute lymphoblastic leukemia, B-cell lymphoma, Burkitt's lymphoma; carcinomas such as lung, breast, bladder, colon, or ovarian cancer; epidermoid cancers, such as malignant melanoma and cancers of the CNS, and other leukemias.

The compounds of the present invention may also be useful as immunosuppressive agents to suppress or inhibit cellular proliferation such as T-cell proliferation associated with organ rejection or the proliferation of NK cells involved in rejection of bone marrow transplants. The compounds of formula (I) may be used to treat autoimmune diseases including, but not limited to, systemic lupus erythematosus, rheumatoid arthritis, non-glomerular nephrosis, psoriasis, chronic active hepatitis, ulcerative colitis, Chrohn's disease, Sjogren's syndrome, Behcet's disease, chronic glomerulonephritis (membranous), chronic thrombocytopenic purpura, allograft rejection and autoimmune hemolytic anemia.

Certain of the compounds of formula I are also useful as intermediates in the preparation of other compounds of formula I. For example, arylhalides can be converted to hydroxymethyl- or hydroxy-aryl compounds by the reaction of the Grignard reagent with ethyl formate or oxygen, respectively, as disclosed in *Org. Synth. Coll. Vol.* 2, 179 (1943) or *J. Amer. Chem. Soc.*, 77, 6032 (1955). Likewise, alkoxy groups can be converted to OH by methods known to the art.

DETAILED DESCRIPTION OF THE INVENTION

Compounds of formula (I) can be prepared by the reaction of methyl cyanoacetate and arylamines or aralkyamines in a suitable solvent such as a lower alkanol at about 50°–100° C. for about 30 min–18 hr. The resultant N-phenyl -or N-phenylalkyl cyanoacetamides, of general formula $(R^4)$ $(R^5)Ph(CH_2)_2NHC(O)CH_2CN$, wherein n, $R^4$ and $R^5$ are defined above, are isolated by cooling and filtering the reaction mixture, in accord with the general procedure of A. Gazit et al., *J. Med. Chem.*, 34, 1896 (1991). The desired 3-(N-phenyl) carbamoyl-2-iminochromenes are prepared by the condensation of variously $R_2$, $R_3$ substituted 2-hydroxybenzaldehydes with the (N-phenyl, or N-phenylalkyl) acetamides in a suitable solvent, e.g., an organic base at 30°–75° C. for about 5 min–5 hr. The reaction mixture is cooled to 20°–25° C. or below, and the compounds of formula (I) are isolated by filtration of the reaction mixture. Synthesis of compounds of formula (I) can also be accomplished as disclosed by T. R. Burke et al., *J. Meal Chem.*, 36, 425 (1993), or by G. Keri et al. (PCT WO/93/16064), by replacing $H_2NC(O)CH_2CN$ with $(R_4)$ $(R^5)Ph(CH_2)_nNHC(O)CH_2CN$ in Scheme III of Burke et al., or as disclosed at pages 5–12 of Keri et al.

Preferably, in the compounds of formula (I), $R^2$ and/or $R^3$ are OH or $OCH_3$; n is 0–2, most preferably O, and $R^4$ and $R^5$ are not both H; most preferably $R^4$ is H and $R^5$ is 2'-, 3'-, or 4'-OH. As used herein, "alkyl" or —$(CH_2)_n$— includes branched and straight chain alkyl groups, as well as cycloalkyl and cycloalkylalkyl. Lower alkyl is preferably $(C_1-C_4)$alkyl.

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, propriolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

As used herein, the term "effective amount" means an amount of compound of the methods of the present invention which is capable of inhibiting the symptoms of the pathological conditions herein described. The specific dose of a compound administered according to this invention will, of course, be determined by the particular circumstances surrounding the case including, for example, the compound administered, the route of administration, the condition of the patient, and the severity of the pathological condition being treated. A typical daily dose will contain a nontoxic dosage level of from about 0.25 mg to about 400 mg/day of a compound of the present invention. Preferred daily doses generally will be from about 1 mg to about 20 mg/day. Dosages can be extrapolated to some extent from the dosages of coumarin shown to be effective against melanoma (50 mg/day). See R. D. Thornes et al., *J. Cancer Res. Clin. Oncol.*, 120 (Suppl.): S 32–34 (1994). Doses found to inhibit rumor growth in murine models, i.e., as disclosed by C. N. O'Callaghan et al., *Proc. R.I.A.*, 79, Sect. B, 87 (1979) can be extrapolated to arrive at dosages for human patients as taught by Borch et al. (U.S. Pat. No. 4,938,949).

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Typically, a formula I compound, or a pharmaceutically acceptable salt thereof, is combined with a pharmaceutically acceptable carrier, diluent or excipient to form a pharmaceutical formulation, or unit dosage form.

The total active ingredients in such formulations comprises from 0.1% to 99.9% by weight of the formulation. By "pharmaceutically acceptable" it is meant that the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginate, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethylene glycols.

The compounds also can be formulated as tablets or in capsules or as elixirs or solutions for convenient oral administration or as solutions appropriate for parenteral administration, for example, by intramuscular, subcutaneous or intravenous routes.

Additionally, the compounds are well suited to formulation as sustained or controlled release dosage forms. The formulations can be so constituted that they release the active ingredient only or preferably in a particular physiological location, optionally over a period of time. The coatings, envelopes, and protective matrices may be made, for example, from polymeric substances or waxes. The compounds can also be delivered via patches for transdermal delivery, s.c. implants, infusion pumps or via release from implanted depot sustained release dosage forms.

The invention will be further described by reference to the following detailed examples, wherein preferred compounds of formula (I) were prepared as shown on Table 1, below:

TABLE 1

Synthesis of 3-(N-phenyl)carbamoyl-2-iminochromenes

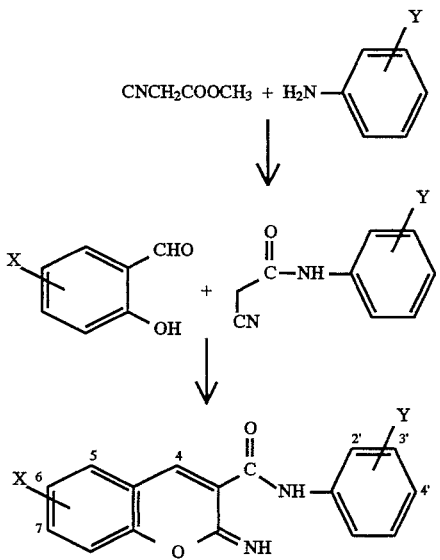

7: X = 6-OH
8: X = 7-OH
9: X = 8-OH
15: X = 7-OCH$_3$
16: X = 6-OCH$_3$
18: X = 7,8-di OH
19: X = 5,7-di OH
25: X = H
32: X = 8-OCH$_3$

T: Y = 4'-OH
TA: Y = 3'-OH
TO: Y = 2'-OH
TABA: Y = 3'-CH$_2$OH
TOBA: Y = 2'-CH$_2$OH
ACTA: Y = 3'-COCH$_3$
AN: Y = H

As shown in Table 1, cyanoacetamides were prepared by the reaction of methyl cyanoacetate with arylamines in ethanol at 70° C. for 0.5–1 hr. N-phenyl-cyanoacetamides were isolated by cooling and filtration of the reaction mixture. The listed 3-(N-phenyl)carbamoyl-2-iminochromenes were prepared by condensation of various derivatives of 2-hydroxybenzaldehyde with (N-phenyl) cyanoacetamides in ethanol containing piperidine at 40° C. to 60° C. for 5 min to 10 min. After cooling, the products were isolated by filtration of the reaction mixture. The melting points and H$^1$NMR spectra of the compounds listed on Table 1 are summarized on Table 2, below.

TABLE 2

| Compounds | mp °C. | $^1$H NMR, ppm |
|---|---|---|
| 7T | 182 | 8.77(1H, s, vinyl)7.26(2H d, J=8.8Hz) 6.72(2H, d, J=8.8Hz)6.95(1H, d, J=2.7Hz) 6.82(2H, d, J=13Hz)6.78(1H. dd, J=2Hz, 11Hz) 9.06(1H, br, s, NH). 7.3(1H, br, s, =NH) 12.5(1H, br, s, OH) |
| 7TA | 170 | 8.77(1H, s, vinyl). 7.19(1H, t, J=7.9Hz) 7.02(1H, d, J=2.7Hz)6.83(1H, dd, J=2.7Hz, 8.84z) 6.69(1H, dd, J=2Hz, 8.1Hz)6.78(1Hdd. J=2.7Hz, 8.4Hz) |
| 8T | 240 | 8.71(1H, s, vinyl), 7.33(1H, d, J=7.3Hz) 7.19(2H, J=8, 7Hz)6.77(2H, J=8.7Hz) 6.33(1H, dd, J=2.1Hz, 8.3Hz)6.24(1H, d. J=2.2Hz). 9.54(br, s,. 1H. NH). 7.4(br, s, 1H=NH) 10.12(1H, s, OH)13.78(1H, s, OH) |
| 8TA | 164° C. | 8.73(1H, s vinyl), 7.4(1H, d, J=8Hz) 6.35(1H, dd, J=2.2Hz, 8Hz)6.26(1H, d, J=2.2Hz) 6.65–7.2(4H, m). 9.7(1H, br, s, NH) |
| 8TO | 270° C. | |
| 9T | 140° C. | 8.84(1H, s, vinyl), 7.0(1H, dd, J=2.2Hz. 7Hz) 6.74(1H, t, J=7.5Hz)6.86(1H, dd, J=2.1Hz, 7.8Hz) 7.28(2H, d, J=8.8Hz). 6.81(2H, d, J=8.8Hz) |
| 9TA | 296° C. | 8.78(1H, s, vinyl). 7.0(1H, d) 6.8–7.4(6H, m) |
| 9TO | 127° C. | 8.94(1h, s, vinyl), 6.69–7.4(7H, m) |
| 9TABA | 223° C. | |
| 9TOBA | 118° C. | |
| 15T | | 8.78(1H, s, vinyl), 7.44(1H, d, J=8.6Hz) 7.23(2H, d, J=8.7Hz)6.79(2H, d, J=8.7Hz) 6.49(1H, dd, J=2.3Hz, 8.5Hz)6.44(1H, d, J=2.2Hz) 3.78(3H, s, CH3O)9.61(1H. br, s,. NH) 7.50(1H, br, s,. =NH). 13.95(1H, s, OH) |
| 16T | | 8.85(1H, s, vinyl), 7.17(1H, d, J=3Hz) 7.3(2H, d, J=8.8Hz)6.8(2H, d, J=8.8Hz) 6.95(1H, dd, J=3Hz. 9Hz). 6.83(1H, d, J=9Hz) 3.72(3H, s, CH3), 9.65(1H, br, s,. NH)12.75(1H, s, OH) |
| 18T | 234° C. | 8.69(1H, s, vinyl). 7.20(2H, d, J=8.7Hz) 6.78(2H, d, J=8.7Hz). 6.86((1H, d, J=8.4Hz) 6.36(1H, d, J=84Hz). 9.51(1H, br, s,. —NH) 7.35(1H, br, s, —NH). 13.95(1H, br s, OH) |
| 18TA | 199.6° C. | 8.70(1H, s, vinyl), 6.90(1H, d. J=8.6Hz). 6.37(1H, d, J=8.6Hz), 6.71(1H, t, J=2Hz) 6.64(1H, dd, J=2Hz, 8.1Hz), 7.20(1H, t, J=8Hz) 7.75(1H, d, J=8.2Hz). 8.1(br, s,. 1H, —NH) |
| 18TO | 199.9° C. | 8.76(1H, s, vinyl). 7.38(1H, dd, J=1.5Hz, 7.9Hz), 7.03(1H, t, J=7.3Hz) 6.93(1H, dd, J=1.4Hz, 8.0Hz), 6.87(1H, t, J=7.6Hz) 6.83(1H, d, J≦8.7Hz), 6.26(1H, d, J=8.6Hz) 9.49(1H, br, s, NH) |
| 18TABA | 149.6 | 8.92(H, s, vinyl)7.27–7.40(3H, m, aromatic) 6.92(1H, dd, J=1.6Hz, J=7.6Hz). 7.09(1H, d, J=7.8Hz) 6.78(1H, d, J=7.8Hz) |
| 18TOBA | | 9.25(1H, br, s, NH) 4.6(2H, s, CH2)4.35(s. 1H, OH) 8.70(1H, s, vinyl). 8.12(1H, br, s,. —NH) 7.49(1H, dd. J=7Hz)7.25–7.32(3H, m) 6.94(1H, d, J=8.4Hz). 6.42(1H. d, J=8.5Hz) 9.8(1H, br, s,. —NH) |
| 18ACTA | 199.4° C. | 8.85(1H, s, vinyl), 8.12(1H, brs, =NH). 7.87(1H, d, J=1.8Hz), 7.82(1H, d. J=7Hz) 7.6(1H, t, J=7.4Hz,. 8.5Hz). 7.2(1H, d, J=8.9Hz) 7.0(1H, d, J=8.6Hz). 6.45(1H, d, J=8.5Hz) 9.8(1H, br, s, NH)3.78(3H, s, CH$_3$) |
| 18AN | 163.3° C. | 10.29(1H, br, s,. —NH)9.8(1H, s, vinyl) 7.05(1H, d, J=7.4Hz), 7.32(1H, d, J=7.4Hz) 7.1–7.6(5H, m, aromatic) |
| 19T | 179.3° C. | 8.34(1H, s, vinyl), 6.38–6.48(6H, m) |
| 19TA | >300 | 8.85(1H, s, vinyl), 9.7(1H, brs, NH), 7.18(1H, t), 5.79–6.78(5H, m) |
| 19TO | 286.5° C. | 8.85(1H, s, vinyl), 7.8(1H, brs, =NH) 9.7(1H, brs, NH), 6.34–6.72(4H, m), 6.36(1H, s)5.75(1H, s) |
| 25T | 138.8 | 8.95(1H, s, vinyl). 7.56(1H, d. J=7.5Hz) 7.35(1H, d. J=7.51Hz), 6.90(2H, m) 7.29(2H, d, J=8.7Hz)6.81(2H, d, J=8.7Hz) 9.7(1H, br, s, NH), 7.6(1H, br, s, =NH) 13.43(1H, s, OH) |
| 25TA | 98.5° C. | |
| 25TO | 187.2° C. | 8.95(1H, s, vinyl), 9.7(1H, brs, NH) 7.5(1H, d), 7.3(2H, m), 7.1(1H, t) 6.8–7.0(4H, m) |

Table 3 shows the inhibitory activities (IC$_{50}$) of several 3-(N-phenyl) carbamoyl-2-iminochromene derivatives on purified tyrosine kinase p60$^{c-src}$ and against five tumor cell lines and human fibroblasts. Purified p60$^{c-scr}$ and Src-family kinases p56$^{lck}$, p56$^{lyn}$, and p55$^{fyn}$ were obtained from Upstate Biotechnology Inc. Kinase assays were performed as described by A. Gezit, *J. Med. Chem.*, 34, 1896 (1991), using poly [Glu,Tyr](4:1) as a substrate.

The source of the cancer cell lines were: HL-60, HT-29, and BT-20, from American Type Culture Collection, Rockville, Maryland; A-1 from Dr. M. H. Freedman, MG-63, from Dr. M. Hurley, and human fibroblast from Dr. R. Zeff. Cells were grown in the culture treated with or without various compounds for 3 days. Cells (except BT-20) were then recovered and treated with Trypan Blue and the number of viable cells counted. For BT-20 cells, a new rapid and simple method using Alamar Blue Assay was used, as described by S. A. Ahmed et al., *J. Immunol. Meth.*, 170, 211 (1994). The symbol i on the Table indicates "not done."

TABLE 3

Structure-Activity Relationship of the 3-(N-phenyl-carbamoyl)-2-iminochromenes (IC$_{50}$, µg/ml)

| Compound | p60$^{c-src}$ | p56$^{lck}$ | p56$^{lyn}$ | p55$^{fyn}$ | IC50 (µg/ml) HL-60 cells | A-1 cells | HT-29 cells | Human fibro-blasts cells | MG-63 | BT-20 |
|---|---|---|---|---|---|---|---|---|---|---|
| 7T | 3.2 | >10 | i | i | 4.2 | 3 | i | i | i | 4.5 |
| 7TA | 1.3 | i | >10 | i | 6.5 | 4.5 | i | i | i | i |
| 8T | 1.2 | >10 | i | i | 5 | 5 | i | i | i | 14 |
| 8TA | 9 | i | >10 | i | 3.3 | i | i | i | i | i |
| 8TO | 0.6 | i | i | i | 8 | i | i | i | i | i |
| 9T | 1.9 | 0.62 | 20 | >20 | 2.5 | 1.9 | 4 | i | 1.25 | 7 |
| 9TA | 0.035 | 0.62 | <10 | 20 | 10 | 6 | 20 | i | i | i |
| 9TO | >10 | 1.2 | >20 | >20 | 1.5 | 1.9 | 4 | i | i | i |
| 18AN | >20 | >20 | >20 | >20 | >20 | 17 | i | i | i | i |
| 18T | 3.6 | 5 | >20 | >20 | 3.5 | 8 | 20 | i | i | 7.2 |
| 18TA | 0.225 | 20 | 18 | >20 | 9 | 20 | >20 | i | i | i |
| 18TO | 12 | 20 | >20 | >20 | 2 | 2 | 15 | i | i | i |
| 19T | 0.2 | 2 | 5 | i | 1 | 1 | 2.5 | >20 | 2.5 | 4 |
| 19TA | 1.25 | 3.75 | 5 | i | 2.5 | 15 | 10 | >20 | 5 | >20 |
| 19TO | 2.1 | i | >>5 | i | 5 | 2.5 | 0.625 | >20 | 2.5 | >20 |
| 25T | >20 | >10 | 10 | i | >10 | i | i | i | i | 10 |
| 25TA | 10 | i | i | i | i | i | i | i | i | i |
| 25TO | >20 | i | i | i | i | i | i | i | i | i |
| 9TABA | 2.5 | i 20 | i | 3 | i | 11 | i | i | >20 | i |
| 9TOBA | 1.8 | i | i | i | 6 | i | i | i | 5 | i |
| 18TABA | 5 | >20 | 20 | >20 | 2.5 | 2.5 | i | i | i | i |
| 18TOBA | 0.9 | 5 | >20 | >20 | 6 | >20 | i | i | i | i |
| 18ACTA | 3 | >20 | 10 | 20 | i | 15 | i | i | i | i |
| 15T | >10 | >10 | i | i | 7.5 | i | i | i | i | >20 |
| 16T | 12.5 | 7.5 | i | i | 5 | i | i | i | i | >20 |
| 32TA | 1.3 | i | i | i | i | 12 | i | i | i | i |

As shown by the data on Table 3, the parent compound, 3-(N-4-hydroxyphenyl) carbamoyl-2-iminochromene (25T) poorly inhibits p60$^{c-src}$ kinase with an IC$_{50}$>20 µg/ml. Mono- or dihydroxylation of the iminochromene ring of the parent compound at positions 5,6,7 or 8 leads to an enhancement of the activity [7T (IC$_{50}$3.2 µg/ml), 8T (IC$_{50}$ 1.2 µg/ml), 9T (IC$_{50}$ 1.9 µg/ml), 18T (IC$_{50}$3.6µg/ml), and 19T (IC$_{50}$ 0.2µg/ml)]. Compound 19T which contains 5,7-dihydroxylation of the iminochromene ring is 200 fold more potent than the parent compound 25T. Substitution of the hydroxyl groups with methoxy groups resulted in a reduction of activity (15T is 8-fold less active than 8T and 16T is 4-fold less active than 7T).

The effects of varying the positions of hydroxyl substitution on the N-phenyl ring of the 3-carbamoyl group were studied. Three compounds containing 8-hydroxylation of the iminochromene ring (9T, 9TA, 9TO) were tested. The compound 9TA, which contains hydroxylation of the N-phenyl ring at 3' position, is 285-fold more potent than the compound 9TO, which contains hydroxylation of the N-phenyl ring at 2'-position. 9TA is 54-fold more potent than the compound 9T, which contains hydroxylation of the N-phenyl ring at the 4-position. Similar results were observed with the compounds 18T, 18TA, and 18TO, which contain 7,8-dihydroxylation of the iminochromene ring but differs in the positions of hyroxyl substitution on the N-phenyl ring: 18T (IC$_{50}$3.6 µg/ml), 18TA (IC$_{50}$ 0.225 µg/ml), and 18TO (IC$_{50}$ 12 µg/ml).

In contrast, compounds containing hydroxymethylation of the N-phenyl ring at 2-position (9TOBA, 18TOBA) are much more potent than their hydroxylated parent (9TOBA and 18TOBA) are much more potent than 9TO and 18TO, respectively).

However, hydroxymethylation of the N-phenyl ring at 3'-position does not produce compounds more potent than their parent hydroxylated compounds (9TABA and 18TABA are not more potent than 9TA and 18TA, respectively).

Compounds containing hydroxylation of the iminochromene ring at 6-position (7T, 7TA), 7-position (8T, 8TA, 8TO), 5 and 7 positions (19T, 19TA and 19TO) or no hydroxylation (25T, 25TA and 25TO) are less sensitive to the effect of varying the positions of hydroxyl substitution on the N-phenyl ring of the carbamoyl group. Compound 18AN which does not contain an hydroxylation group on the N-phenyl ring is inactive (IC$_{50}$>20 µg/ml).

Hydroxylation of the N-phenyl ring at 3'-position produces the compound 18TA which is 88-fold more potent than 18AN. Acetoxylation of the 3'-position of compound 18TA produced 18ACTA which is 13-fold less potent than 18TA. The most active compound 9TA (IC$_{50}$0.035 µg/ml) which is hydroxylated at 3°-and 8-positions.

Several compounds were also examined for their selectivity against other tyrosine kinases of the Src family including lck, lyn and fyn. The compounds were relatively weak inhibitors for these kinases. The pattern of structure-activity relationship observed with p60$^{c-src}$ was not reproduced with these kinases.

As shown on Table 3, several compounds of formula (I) were tested for their ability to inhibit the growth of human cancer cells including promyelocytic leukemia HL-60 cells (S. J. Collins et al., *Blood*, 70, 1233 (1987)); acute lymphocytic leukemia A-1 cells, (S. Kamel-Reid et al., *Leukemia*, 6, 8 (1992)); human osteosarcoma MG-63, (A. Pirskanen et al., *J. Bone and Mineral Res.*, 1635 (1994)); human breast carcinoma BT-20 (G. G. Castles et al., *Cancer Res.*, 58, 5934 (1992)); and human colon adenocarcinoma HT-29 cells (R. Garcia et al., *Oncogene*, 6, 1983 (1991)).

Surprisingly, compounds which show a strong inhibitory effect against p60$^{c-src}$ (e.g., 9TA and 18TA) are not as potent against these cell lines as some of the compounds with relatively weak activity against p60$^{c-src}$ (e.g., 9TO and 18TO). Also, the pattern of structure-activity relationship observed with HL-60 cells was not reproduced in other cell lines. For the HT-29 cells, 19TO appeared to be most effective ($IC_{50}$ 0.625 μg/ml). For the HL-60, MG-63, BT-20, and A-1 cells, 19T appeared to be the most potent compound ($IC_{50}$ 1 μg/ml). Compounds which are inactive ($IC_{50}$>20 μg/ml) against $p60^{c-src}$ (e.g., 18AN, 25T) are also less active in inhibiting cell growth. The most effective compounds for inhibiting cancer cell growth, 19T, 19TA and 19TO are not effective in inhibiting the growth of human fibroblast cells ($IC_{50}$ >20 μg/ml), thus demonstrating their ability to discriminate between cancerous and normal cells.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of inhibiting proliferation of a population of mammalian cells which express protein tyrosine kinase $p60^{c-src}$ comprising contacting said cells with an effective amount of a compound of formula (I)

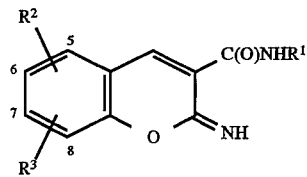

wherein $R^2$ is H, OH, halo or $O(C_1-C_4)$alkyl; $R^3$ is OH, halo, or $O(C_1-C_4)$alkyl; and $R^1$ is

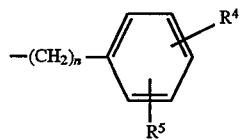

wherein n is 0–12; $R^4$ is H, OH, halo, $O(C_1-C_4)$alkyl, $CH_2OH$, $CO_2N(R)_2$, wherein each R is H or $(C_1-C_4)$alkyl, or $C(O)R^6$ wherein $R^6$ is OH or $O(C_1-C_4)$alkyl; and $R^5$ is OH, halo, $O(C_1-C_4)$alkyl, $CH_2OH$, $CO_2N(R)_2$, or $C(O)R^6$; or a pharmaceutically acceptable salt thereof, wherein the amount is effective to inhibit said $p60^{c-src}$.

2. The method of claim 1 wherein n is 0.

3. The method of claims 1 or 2 wherein $R^4$ is H or OH and $R^5$ is OH.

4. The method of claim 3 wherein $R^4$ is OH and $R^5$ is OH.

5. The method of claims 1 or 2 wherein $R^2$ is H or OH and $R^3$ is OH.

6. The method of claim 5 wherein $R^2$ is OH.

7. The method of claim 1 wherein $R^2$ is H and $R^3$ is $OCH_3$.

8. The method of claim 1 wherein $R^4$ is H and $R^5$ is $CH_2OH$.

9. The method of claim 1 wherein the cells are cancer cells.

10. The method of claim 9 wherein the amount is administered to a human cancer patient.

11. The method of claim 10 wherein the cancer is selected from a carcinoma or a leukemia.

12. The method of claim 10 wherein the cancer is acute lymphoblastic leukemia, B-cell lymphoma, Burkitt's lymphoma, lung cancer, breast cancer, bladder cancer, ovarian cancer, or colon cancer.

13. The method of claim 1 wherein the amount is administered to a human patient afflicted with an autoimmune disease.

14. A compound of the formula (I):

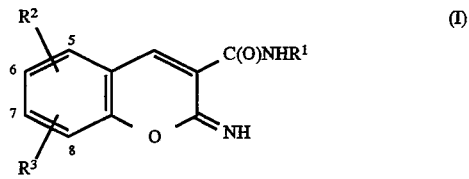

wherein $R^2$ is H, OH, halo, or $O(C_1-C_4)$alkyl, $R^3$ is OH, halo, or $O(C_1-C_4)$alkyl; $R^1$ is

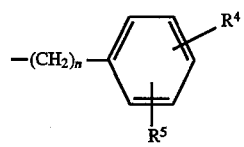

wherein n is 0–12; $R^4$ is H, OH, halo, $CH_2OH$, $C(O)CH_3$, $C(O)N(R)_2$ wherein each R is H or $(C_1-C_4)$alkyl; or $C(O)R^6$ wherein $R^6$ is OH or $O(C_1-C_4)$alkyl; and $R^5$ is OH, $CH_2OH$, $C(O)CH_3$, $C(O)N(R)_2$ or $C(O)R^6$; with the proviso that when one of $R^2$ and $R^3$ is H and the other is $O(C_{1-C4})$alkyl, $R^4$ is H and $R^5$ is OH or halo, the OH or halo is not 2'-OH or 2'-halo; or a pharmaceutically acceptable salt thereof.

15. The compound of claim 14 wherein n is 0.

16. The compound of claims 14 or 15 wherein $R^2$ is H or OH and $R^3$ is OH.

17. The compound of claim 16 wherein $R^2$ is OH.

18. The compound of claims 14 or 15 wherein $R^4$ is H or 3'-OH, 4'-OH, or 5'-OH and $R^5$ is 3'-OH, 4'-OH, or 5'-OH.

19. The compound of claim 18 wherein $R^4$ is 3'-OH, 4'-OH, or 5'-OH.

20. The compound of claim 14 wherein $R^2$ is H and $R^3$ is $OCH_3$.

21. The compound of claim 14 wherein $R^4$ is H and $R^5$ is $CH_2OH$.

22. The compound of claim 14 halo is bromo or chloro.

23. The compound of claim 22 wherein $R^2$ is H and $R^3$ is bromo or chloro.

24. A pharmaceutical composition comprising a compound of claim 14 combination with a pharmaceutically acceptable carrier.

* * * * *

UNITED STATES PATENT AND TRADEMARK OFFICE
CERTIFICATE OF CORRECTION

PATENT NO. : 5,648,378

DATED : July 15, 1997

INVENTOR(S) : Chi-Kuang Huang

It is certified that error appears in the above-identified patent and that said Letters Patent is hereby corrected as shown below:

In column 2, line 67, it should read $C_1$-$C_4$.

In columnn 3, line 8, it shoud read $C_1$-$C_4$.

In column 12, line 53, please insert --in-- after 14.

Signed and Sealed this

Sixth Day of January, 1998

*Attest:*

BRUCE LEHMAN

*Attesting Officer*  *Commissioner of Patents and Trademarks*